United States Patent [19]

Kinnersley et al.

[11] Patent Number: 5,593,947
[45] Date of Patent: *Jan. 14, 1997

[54] METHOD FOR MORE EFFICIENT UPTAKE OF PLANT GROWTH NUTRIENTS

[75] Inventors: Alan M. Kinnersley, Knoxville, Tenn.;
Larry P. Koskan, Orland Park, Ill.;
David J. Strom, New Market, Tenn.;
Abdul R. Y. Meah, Justice, Ill.

[73] Assignee: Donlar Corporation, Bedford Park, Ill.

[*] Notice: The term of this patent shall not extend beyond the expiration date of Pat. No. 5,350,735.

[21] Appl. No.: 313,436

[22] Filed: Sep. 27, 1994

Related U.S. Application Data

[63] Continuation-in-part of Ser. No. 972,375, Nov. 5, 1992, Pat. No. 5,350,735.
[51] Int. Cl.⁶ .......................... A01N 43/36; A01N 59/06; A01N 37/30
[52] U.S. Cl. .......................... 504/283; 504/320; 504/192
[58] Field of Search .......................... 504/147, 121, 504/125, 320, 283, 192

[56] References Cited

U.S. PATENT DOCUMENTS

| | | | |
|---|---|---|---|
| 4,172,072 | 10/1979 | Ashmead | 260/115 |
| 4,799,953 | 1/1989 | Danzig et al. | 71/98 |
| 4,813,997 | 3/1989 | Kinnersley et al. | 71/66 |
| 4,839,461 | 6/1989 | Boehmke | 528/363 |
| 4,863,506 | 9/1989 | Young | 71/113 |
| 4,863,898 | 9/1989 | Ashmead et al. | 514/6 |
| 5,059,241 | 10/1991 | Young | 71/106 |
| 5,350,735 | 9/1994 | Kinnersley et al. | 504/147 |

OTHER PUBLICATIONS

Kinnersley et al., Plant Growth Regulation 9:137–146 (1990).

Byrnes, Fertilizer Research 26:209–215 (1990).

*Primary Examiner*—José G. Dees
*Assistant Examiner*—Brian Bembenick
*Attorney, Agent, or Firm*—Olson & Hierl, Ltd.

[57] ABSTRACT

Water-soluble polyorganic acids having a molecular size of more than 1,500 Daltons enhance plant fertilizer uptake when supplied to the plant, usually in the root feeding zone or through foliar mechanisms. Particularly suitable for this purpose are the polyamino acids such as polyaspartic acid and copolymers thereof.

8 Claims, 3 Drawing Sheets

CONTROL
FULL FERTILIZER

DGI - K1 - (10ppm)
FULL FERTILIZER

CONTROL
FULL FERTILIZER

DGI - K1 - (10ppm)
1/3 FERTILIZER

METHOD FOR MORE EFFICIENT UPTAKE OF PLANT GROWTH NUTRIENTS

CROSS-REFERENCE TO RELATED APPLICATION

This application is a continuation-in-part of U.S. Ser. No. 07/972,375, filed on Nov. 5, 1992, now U.S. Pat. No. 5,350,735.

TECHNICAL FIELD

This invention relates to the consolidation and collection of plant growth nutrients and availing them for absorption, uptake and utilization by germinating or growing plants resulting in more efficient usage of these nutrients. More particularly, this invention relates to chemical absorption phenomena that facilitate the collection of nutrients for assimilation by plants through either seed, root or foliar mechanisms.

BACKGROUND OF THE INVENTION

Organic acids and oligomers thereof have been shown to promote plant growth. Typical such promoters of plant growth are described by Kinnersley et al., Plant Growth Regulation 9:137–146 (1990), which publication mentions the effects of lactic acid and relatively low molecular weight oligomers of lactic acid on plant growth. Similar description is found in U.S. Pat. No. 4,813,997 to Kinnersley et al. (oligomers of glycolic and/or L-lactic acid) and U.S. Pat. No. 4,799,957 to Danzig et al. (oligomers of thiolactic and thioglycolic acids). All of the forgoing approaches to plant growth promotion appear to focus on coordination as a means for increasing plant uptake of compounds vital to the growth of the plant, e.g., micronutrients such as calcium, magnesium, sulfur, manganese, zinc, copper, iron, boron, and the like.

A very common approach to the promotion of plant growth has been, and continues to be, the use of nutrients (fertilizers), natural as well as synthetic. The latter usually provides nitrogen in a plant-usable form, such as urea for example, and/or inorganic nitrates, phosphates, or the like compounds. While such nutrients may be applied, more or less, at the convenience of the farmer, and may be applied as often as deemed desirable, the overuse of synthetic nutrients and the inefficient use of synthetic nutrients are major factors responsible for environmental problems such as eutrophication of ground water, nitrate pollution, phosphate pollution, and the like. An overview of the undesirable effects of nitrogen fertilizer is presented by Byrnes, Fertilizer Research 26:209–215 (1990).

To ameliorate the problems attendant to inefficient nutrient use and nutrient overuse, it would be desirable and necessary for environmental and production reasons to improve the collection, absorption and consolidation of plant nutrients and hold them in a condition and position to maximize availability for plant uptake while minimizing loss of nutrients or fertilizer elements through leaching, denitrification, vaporization and other mechanisms that distort or prevent assimilation of these nutrients by plant biological and physical mechanisms. The present invention addresses these problems, and provides methods for collecting or attracting plant nutrients which results in more efficient usage of nutrients in the growing plant.

SUMMARY OF THE INVENTION

Enhanced plant productivity as demonstrated by increased growth rate, increased biomass, higher yields and quality (protein content), accelerated rate of root formation, increased tillering, increased chlorophyll concentration and the like indicia, is achieved by more efficient nutrient utilization by making available to the plant a higher level of plant food nutrients in the root feeding zone or through absorption and translocation through foliar mechanisms via a polyaspartic acid that is water soluble and not absorbed into the plant, i.e., having a weight average molecular weight (Mw) larger than 1500. Such polyaspartic acids are non-aromatic polymers that have at least 15 repeating amino acid units or mers in the polymer chain. The polyaspartic acid can be supplied to the plant directly or as a polysuccinimide which hydrolyzes in situ to polyaspartic acid.

Particularly preferred for the present purposes are polymers such as polyaspartic acid or polysuccinimide alone or in combination with other polymers, e.g., polylactic acid, polyglycolic acid and the like, and other water-soluble polycarboxylates, e.g., polyacrylic acid, polymaleic acid, their copolymers and the like. Other water soluble polymers such as polyacrylamide and acrylamide-acrylic acid copolymers can also be used in combination with the polyaspartic acids.

Polysuccinimide and polyaspartic acids useful in this invention are represented by the following structures:

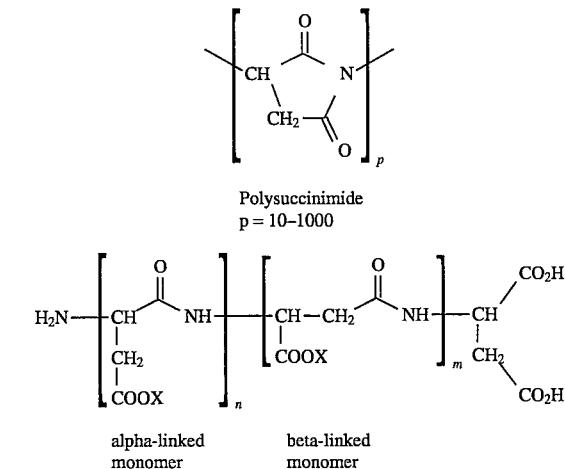

Polysuccinimide
p = 10–1000 alpha-linked monomer    beta-linked monomer where $X=H^+$, $Na^+$, $NH_4^+$, $K^+$, $Ca^{++}$, $Mg^+$, $Zn^{++}$, $Co^{++}$, $Li^+$, $Ba^{++}$, $Fe^{++}$ and $Fe^{+++}$; $n+m \geq 15$.

The polyaspartic acid moieties contain aspartic acid monomer units linked by α peptide and β peptide bonds. A preferred polyaspartic acid is β-polyaspartic acid, i.e., one having >50 mole % of aspartic acid units linked by β peptide bonds and <50 mole % of aspartic acid units linked by αpeptide bonds. Preferably, 60–80 mole % of the polyaspartic acid is in β-linkage form and the polyaspartic acid has an Mw within the range of 2000–100,000. More preferably, approximately 70 mole % to 80 mole % of the polyaspartic acid has β form and has a Mw within the range of 2000–20,000. Most preferably, approximately 70 mole % to 75 mole % of the polyaspartic acid has β form and 25 mole to 30 mole % α, and has Mw within the range of 2000–5000.

BRIEF DESCRIPTION OF THE DRAWINGS

In the drawings, there are shown photographic reproductions of corn plants treated in a particular manner alongside a control corn plant. In each case a yardstick (36 inches) is shown positioned between the photographed plants to indicate scale. In particular.

DETAILED DESCRIPTION OF PREFERRED EMBODIMENTS

Figure 1:
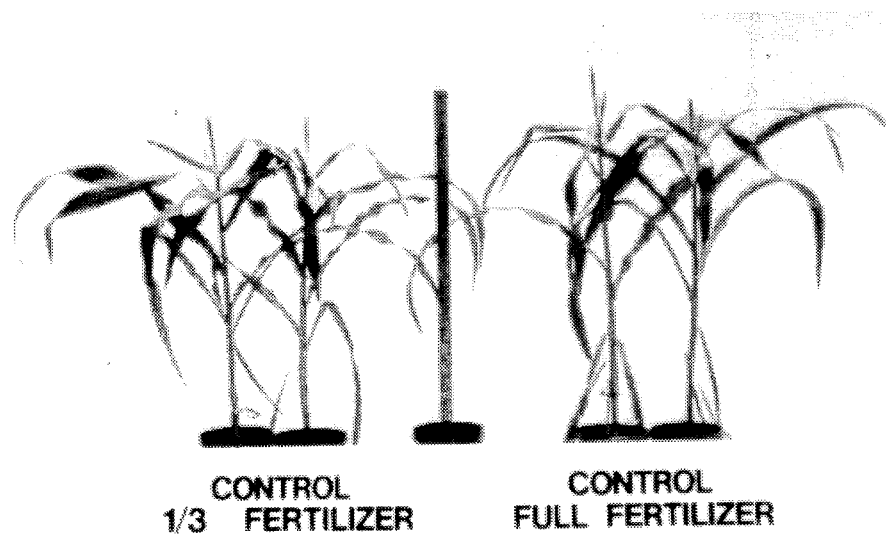
FIG. 1 shows corn plants 40 days after planting, and treated with one-third of the recommended fertilizer dosage alongside a corn plant treated with the recommended dosage for the same fertilizer.
Figure 2:
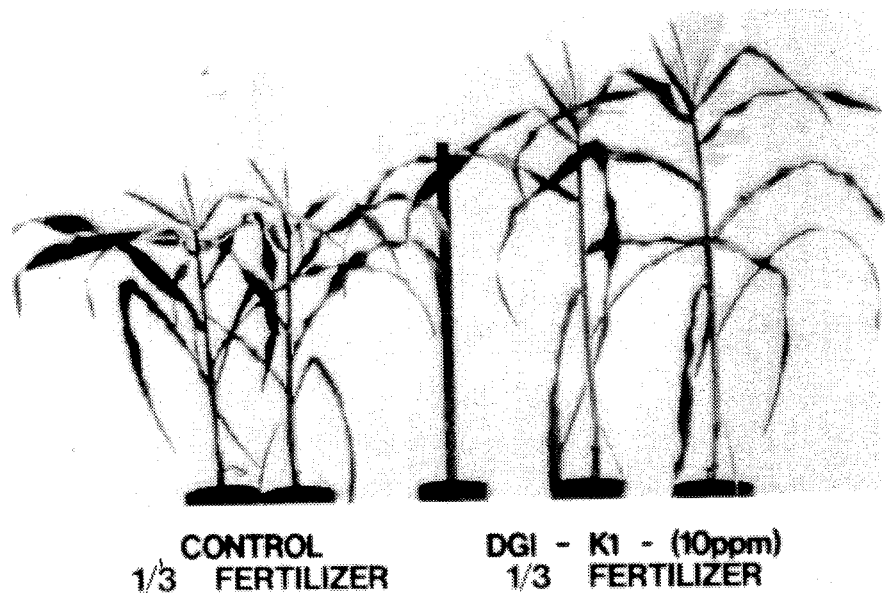
FIG. 2 shows a corn plant 40 days after planting, one treated with one third of the recommended fertilizer dosage alongside a corn plant similarly treated with the same fertilizer but also with 10 parts per million by weight of polyaspartic acid.

The present invention, in its various aspects, is predicated on the discovery that polymeric organic acids that are of a too large molecular size to enter a plant but can nevertheless, within their entity, collect, attract and hold chemical molecules (nutrients) so as to make them efficient to the plant in a more available and ready manner, thereby allowing plant growth with a more efficient use of applied and natural chemical materials. The more efficient utilization of such nutrients can be realized in the presence of the polymeric amino acid inasmuch as relatively lower nutrient dosages can be relied upon to provide the requisite nutrients to the plant.

In general, the polymeric organic acids can be made available to the plant as nutrient solutions containing at least about 10 parts per billion (ppb) by weight, preferably about 0.1 to about 1,000 parts per million (ppm) by weight, more preferably about 1 to about 500 ppm by weight, of the polymeric amino acid in the solution. Such solutions can be applied to the soil surrounding the plant so as to contact the plant's root system, can be applied to the plant's foliage utilizing usual foliar feeding techniques, can be introduced into hydroponic gardening or farming systems, and in any other convenient manner. Solutions containing the polymeric amino acid can be sprayed or otherwise applied to contact the roots, stems, or leaves of the plants whose growth and/or development is to be enhanced, as well as to the seeds or reproduction parts of these plants, in an amount as is discussed in greater detail hereinbelow. Solutions containing the polymeric amino acid are also useful to enhance effective plant growth under growth limiting conditions, e.g., in soil that contains salts in concentrations normally toxic to plants, soil depleted in certain nutrients, etc.

The polymeric amino acids such as polyaspartic acid can also be applied to soil in solid form alone or in combination with nutrients. Granular, pelletized, dust or powdered forms of the polyamino acids can be applied by gravity or air blast equipment into the furrow, row or site at seeding or planting time. Dry granular or pelleted forms of the polyamino acids such as polyaspartic acid can be impregnated or pre-formed as carriers of nutrients and can then be used for surface application by ground rig or aircraft.

The polymeric amino acids can be applied to soil as a solid in the anhydro form as for example anhydropolyaspartic acid (polysuccinimide). Polysuccinimide can be mixed with sodium carbonate or sodium bicarbonate and applied as a powder, as a dry granule or in pellet form. The sodium carbonate and sodium bicarbonate will hydrolyze polysuccinimide to polyaspartic acid sodium salt in moist soil. Polysuccinimide can also be applied to soil as a powder, pellet or as granules mixed with limestone (Ca and Mg carbonate). In this application the carbonates of the limestone can hydrolyze the polysuccinimide to polyaspartic acid sodium salt in moist or wet soil. Another way of using polysuccinimide is to apply it to soil as a powder, granule or pellet after the soil has received an injection of ammonia. In this process, ammonium hydroxide formed from the ammonia and water in the soil will hydrolyze the polysuccinimide to polyaspartic acid.

The polymeric amino acids, to be suitable for the practice of the present invention, must be or becomes water soluble, non-aromatic, and must have a molecular size sufficiently large to preclude absorption into the plant's own system. To that end, the non-aromatic polymeric organic acids deemed suitable for the present purposes, while hydrophilic, have a weight average molecular weight (Mw) larger than 1,500 and have at least about 15 repeating organic acid units (residues), or mers, in the linear polymer chain that constitutes the polymeric acid. Such linear polymer chains can be cross-linked, if desired, but only to a degree that does not materially affect the water solubility of the polymeric moiety. Polymeric organic acids having a molecular size in excess of Mw about 100,000 usually do not exhibit adequate solubility in water for the present purposes, thus for present purposes a polymeric amino acid molecular size not larger than Mw about 100,000 is preferred. Particularly preferred molecular size is in the range of Mw about 2,000 to about 30,000.

Illustrative are polymeric amino acids, with or without carboxylic acid, thiocarboxylic acid, mercapto, hydroxy, imidocarboxy, and/or amino side chains, such as, for example, polylysine, polyglutamic acid, polysuccinimide, polyaspartic acid, polyglycine, polycysteine, polycysteine/ glutamic acid, polyserine, polycysteine/glutamic/aspartic acid, mixtures of the foregoing, and the like. Block or random copolymers or terpolymers of several amino acids are also within the purview of the present invention as the polymeric acid component thereof. For example, the utilized polymeric acid component can be a block copolymer of aspartic acid residues and L-lactic acid residues, a random copolymer of aspartic acid residues and glycolic acid residues, a conjugated protein constituted by amino acid residue chains interconnected by one or more polycarboxylic acid residues, a copolymer containing succinimide residues and partially hydrolyzed polysuccinimide. The polymeric amino acids of this invention can be used in combination with other water soluble organic polymers to provide more efficient utilization of both natural and synthetic plant growth nutrients. Examples of water soluble polymers which can be used are: polylactic acid, polyglycolic acid, polyacrylic acid, polymaleic acid, polyacrylamide, acrylamide-acrylic acid copolymers, poly(vinyl alcohols), acrylamide/2-acrylamido-2-methylpropanesulfonic acid copolymers, acrylamide/daillyldimethylammonium chloride copolymers, acrylamide/ dimethylaminoethyl methacrylate and acrylate copolymers and methyl chloride or sulfate quaternized derivatives of these copolymers, polyvinylpyrrolidone, acrylic acid/maleic acid copolymers, polyitaconic acid, acrylic acid/itaconic acid copolymers, maleic acid/itaconic acid copolymers, polymethacrylic acid, methacrylic acid/acrylamide copolymers and methacrylic acid/acrylic acid copolymers.

The water soluble polymers which can be used in combination with the polyamino acids should have a molecular size larger than Mw of 1500 and have at least about 15 repeating organic monomer units, or mers, in the linear polymer chain that constitutes the water soluble polymer. Such linear polymer chains can be cross-linked, if desired, but only to a degree that does not materially affect the water solubility of the polymeric moiety. For present purposes, a water soluble polymer of molecular size not larger than Mw of about 100,000 is preferred. Particularly preferred molecular size is in the range of Mw about 2,000 to about 30,000. Polymeric amino acids for use in the present invention can be made, inter alia, by thermal condensation methods. See, for example, U.S. Pat. No. 5,057,597 to Koskan, U.S. Pat. No. 5,221,733 to Koskan et al.; U.S. Pat. No. 5,219,952 to Koskan et al.; Little et al., American Chemical Society 97:263–279 (1991), and U.S. Pat. No. 4,696,981 to Harada et al.

The starting materials for the polymerization, i.e., the amino acids, can exist as optical isomers, depending upon their respective structures, and can be polymerized either as a racemic mixture or as segregated optical isomers.

Hydrophobic polymeric amino acids such as polyalanine or other non-hydrolyzed water insoluble polyamino acids are not suitable.

Particularly well suited for the practice of the present invention are the non-chelating polyamino acids such as polyaspartic acid having a molecular weight (Mw) in the range of about 3,000 to about 100,000, polyglutamic acid having a molecular weight (Mw) in the range of about 4,000 to about 14,000, polyglycine having a molecular weight (Mw) in the range of 1,500 to about 7,000, and polylysine having a molecular weight (Mw) in the range of about 2,000 to about 7,000.

The presently contemplated polyamino acids are not chelating agents, and as such do not form chelates with the plant nutrients. Moreover, the presently contemplated polyamino acids are not considered plant growth regulators.

The aforesaid polyamino acids can function to increase the efficiency of utilization of nutrients, both natural and synthetic, by providing a nutrient attracting and collecting environment which allows more nutrients within the plant absorption zone to be available for uptake and utilization. The nutrients which are more efficiently utilized can be those found naturally in the soil or plant growing medium or those added to promote plant growth or residual nutrients from previous nutrient treatments. More efficient utilization by the growing plants of both macronutrients (N, P, K) and micronutrients (Ca, Mg, S, Zn, Fe, Mn, B, Co, Mo, Cu, Ni) is accomplished by employing the polyamino acids of this invention.

There are many uses and applications for the present inventions in its various aspects. Illustrative are uses in agriculture, gardening, horticulture, hydroponics, forestry, land reclamation (e.g., landfills, soils with relatively high salt concentration, etc.), and the like.

Suitable dosage rates for soil treatment with the polymeric amino acid component of the present invention, so as to provide a sufficient polymeric amino acid to the plant to collect and hold nutrient in the plant utilization range, are about 2 to about 500 ounces of the polymeric amino acid per acre. Crops with an abundance of foliage, such as wood crops, grain crops, cotton, etc., usually are treated at dosage rates in an intermediate range, i.e., about 25 to about 250 ounces per acre. Relatively lower dosage rates within the foregoing overall range, i.e., about 2 to about 25 ounces per acre, usually are sufficient for agricultural row crops, flowering nursery crops, and the like.

The polymeric amino acid is made available to the plant as a separate treatment, or in combination with other water soluble polymers or in combination with other nutrients. Solid as well as liquid dosage forms can be utilized for this purpose, e.g., aqueous solutions, solid soil conditioning substances such as particulate clays bearing the polymeric amino acid commingled with nutrient components, solid particulate admixtures of polymeric amino acid, nutrient and the like.

The polymeric amino acid can be made available to the plant in the anhydro form as for example anhydropolyaspartic acid (polysuccinimide) in combination with a basic material which in the presence of water, soil moisture, rainfall, etc. can hydrolyze polysuccinimide to polyaspartic acid or salts. Basic materials which can be used are sodium carbonate, sodium bicarbonate, limestone, ammonia and the like. Polysuccinimide can be applied and mixed with the solid basic material in powder, pellet or granule form. Similarly, powder, pellet or granule form of polysuccinimide can be applied to soil after an injection of ammonia has been done.

A polyamino acid which is well suited for the practice of this invention, to provide more efficient utilization of both natural and synthetic plant growth nutrients, is polyaspartic acid. This polymer can be conveniently prepared from L-aspartic acid, D-aspartic acid or DL-aspartic acid, or from aspartic acid precursors (ammonium maleate, maleamic acid, ammonium malate, diammonium maleate, diammonium malate, ammonium maleamate, ammonium fumarate, diammonium fumarate) using thermal condensation methods.

DEFINITIONS

The term polyaspartic acid used herein also includes salts of polyaspartic acid. Counterions for polyaspartate include, but are not limited to, the alkaline and alkaline earth cations some examples of which are $Na^+$, $K^+$, $Mg^+$, and $Li^+$, $Ca^{++}$, $Zn^{++}$, $Ba^{++}$, $Co^{++}$, $Fe^{++}$ and $Fe^{+++}$, and $NH_4^+$.

Polysuccinimide is the imide form of polyaspartic acid and is also known as anhydropolyaspartic acid.

The term "chelate," as used herein in its various forms, refers to a complex formed by a polydentate ligand, i.e., a ligand that supplies more then one pair of electrons to a cation. See, for example, Masterson et al., *Chemical Principles*, 6th ed., Saunders College Publishing Co., Philadelphia, Pa. (1985), p. 635.

Similarly, the term "chelating agent," as used herein in its various forms, refers to a ligand that possesses at least two pairs of unshared electrons which pairs are far enough removed from one another to give a ring structure with a stable geometry. Ibid, p. 638.

The present invention is further illustrated by the following examples which demonstrate more efficient utilization of plant growth nutrients by employing polyaspartic acid (PA).

EXAMPLE 1

More Efficient Usage of Nutrients in Corn Plants

White corn (Early Sunglow; George W. Park Seed Co., Greenwood, S.C.) was grown in a greenhouse in one gallon pots filled with Fafard 3B potting soil. To each pot was added Peters™ 20-20-20 fertilizer in an amount representing a full dose of nutrients or a ⅓ dose of nutrients. A portion of the pots so treated also received an aqueous solution of (PA) (50 ml; 10 ppm by weight of PA having a molecular weight (Mw) of about 3,000–5,000. The growth rates of the white corn plants in these pots were monitored, and representative plants were photographed 40 days after planting. These photographs are depicted in FIGS. 1 through 4.

Figure 3:
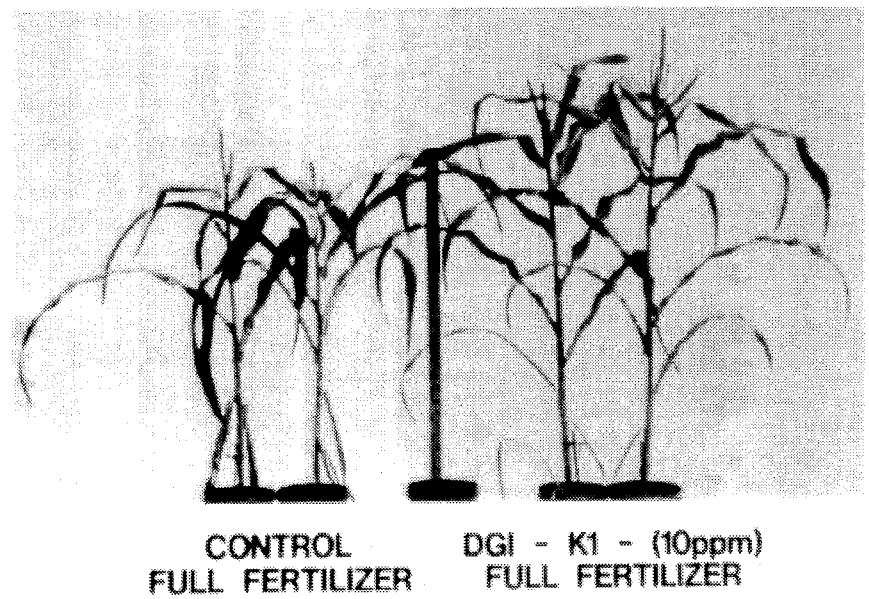
FIG. 3 shows corn plants 40 days after planting, both treated with the recommended fertilizer dosage and one plant also with 10 parts per million by weight of polyaspartic acid.
Figure 4:
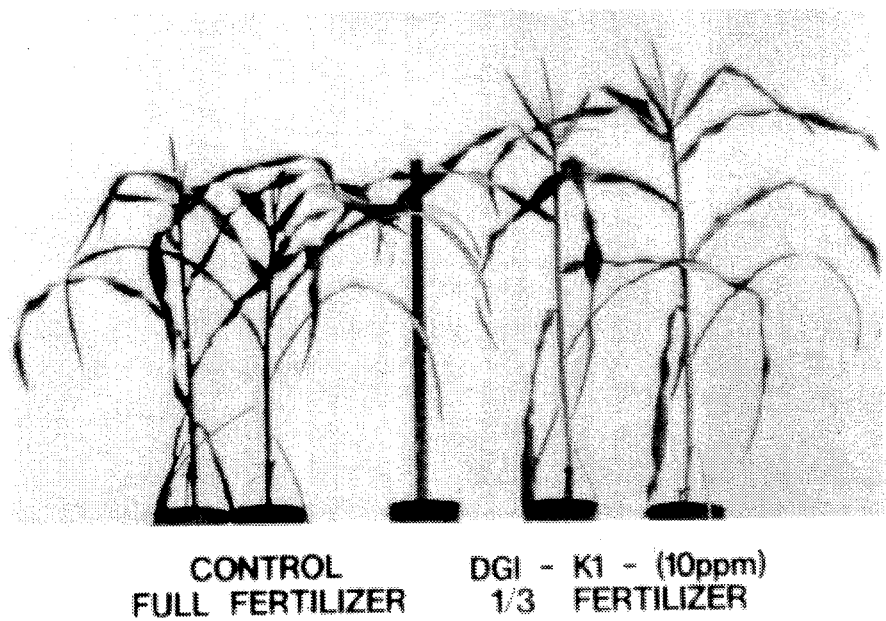
FIG. 4 shows corn plants 40 days after planting, one treated with the recommended fertilizer dosage and the other with one-third of the recommended fertilizer dosage but also with 10 parts per million by weight of polyaspartic acid.

These Figures show that the availability of polyaspartic acid to the plant enhances plant growth at a reduced nutrient level, i.e., corn plants treated at one-third of the nutrient level but with 10 ppm of polyaspartic acid added (FIG. 4) show greater growth than corn plants will the full amount of nutrient. Corn plants grown using the full nutrient level also undergo enhanced growth when 10 ppm of polyaspartic acid is used along with the nutrient (FIG. 3). Both experiments demonstrate a more efficient utilization of nutrients for plant growth.

EXAMPLE 2

Effects of Polyaspartic Acid on Growth Patterns of Corn Plants With No Added Fertilizer White corn (Early Sunglow; George W. Park Seed Co., Greenwood, S.C.) was grown in a greenhouse in one gallon pots filled with Fafard 3B potting soil. No fertilizer was added to each pot. A portion of the pots so treated received aqueous solutions of polyaspartic acid of varying dosage levels (50 ml of solution; 1 ppm, 10 ppm, 100 ppm, and 1000 ppm of PA having a molecular weight (Mw) of about 3000–5000. The growth rates of the white corn plants in these pots were monitored on a weekly basis and the data is shown in Table I, below.

TABLE I

GROWTH PATTERNS OF EARLY SUNGLOW CORN; NO ADDED FERTILIZER; SINGLE TREATMENT

| Dosages of PA | Height Change (inches) | | | |
|---|---|---|---|---|
| | Week 1 | Week 2 | Week 3 | Week 4 |
| Control (No PA) | 13.0 | 9.0 | 6.4 | 5.2 |
| 1 ppm | 12.5 | 9.4 | 5.4 | 5.7 |
| 10 ppm | 11.6 | 11.0 | 5.0 | 7.0 |
| 100 ppm | 11.4 | 10.4 | 6.4 | 7.2 |
| 1000 ppm | 10.4 | 10.4 | 5.6 | 7.8 |

The data shown in Table I indicates that after one week of growth, corn plants with no added fertilizers but with polyaspartic acid (PA) added in dosages of 1 to 1000 ppm received no benefit from polyaspartic acid treatment. After week 2 of corn plant growth a beneficial effect was shown at all four dosage levels of polyaspartic acid. After three weeks of growth, only the 100 ppm dosage level of polyaspartic acid shows a benefit over no PA treatment. Finally after four weeks of corn plant growth, a low level of plant growth was occurring but increased growth rate was observed with all four dosage levels of polyaspartic acid. In summary, during the initial stage (first week) of corn plant growth polyaspartic acid did not increase growth rate without added fertilizer. However, after the next three weeks of growth of the plant, polyaspartic acid treatment was beneficial to plant growth even without added fertilizer. These results indicate that more efficient utilization of existing nutrients in the soil has occurred.

EXAMPLE 3

Effects of Polyaspartic Acid on Potassium Uptake in Early Sunglow Corn With No Added Fertilizer White corn (Early Sunglow; George W. Park Seed Co., Greenwood, S.C.) was grown in a greenhouse in one gallon pots filled with Fafard 3B potting soil. No fertilizer or potassium source were added to the pots. The pots were treated with varying dosages of polyaspartic acid Ms 3,000–5,000, as in Example 2. After a 40 day growing period, the plants were harvested and potassium content of the plants was determined.

TABLE II

EFFECT OF POLYASPARTIC ACID ON POTASSIUM UPTAKE; EARLY SUNGLOW CORN; NO ADDED FERTILIZER; SINGLE TREATMENT/SOIL

| Dosage of Polyaspartic Acid Used | % Potassium In Corn Plants | % Increase of Potassium In Corn Plants |
|---|---|---|
| 0 ppm | 2.6 | — |
| 1 ppm | 2.7 | 3.8 |
| 10 ppm | 3.0 | 15.4 |
| 100 ppm | 2.8 | 7.7 |
| 1000 ppm | 3.2 | 23.1 |

The data reported in Table II shows that a more efficient uptake of potassium by the corn plants resulted when polyaspartic acid was used without added fertilizer. At the 1000 ppm dosage level, a 23.1% increase in potassium content was found in the corn plants.

EXAMPLE 4

Effect of Polyaspartic Acid on Phosphorous Uptake in Early Sunglow Corn With No Added Fertilizer White corn (Early Sunglow; George W. Park Seed Co., Greenwood, S.C.) was grown in a greenhouse in one gallon pots filled with Fafard 3B potting soil as in Examples 2 and 3. No fertilizer or phosphorus containing compounds were added to the pots. The pots were treated with varying dosages of polyaspartic acid (Mw 3000–5000) as in Examples 2 and 3. After a 40-day growing period, the plants were harvested and phosphorus content of the plants was determined. Results from this study are shown in Table III, below.

TABLE III

EFFECT OF POLYASPARTIC ACID ON PHOSPHORUS UPTAKE; EARLY SUNGLOW CORN; NO ADDED FERTILIZER; SINGLE TREATMENT/SOIL

| Dosage of Polyaspartic Acid Used | % Phosphorus In Corn Plants | % Increase of Phosphorus In Corn Plants |
|---|---|---|
| 0 ppm | 0.3 | — |
| 1 ppm | 0.36 | 20.0 |
| 10 ppm | 0.34 | 13.3 |
| 100 ppm | 0.38 | 26.7 |
| 1000 ppm | 0.44 | 46.7 |

The results listed in Table III show that use of polyaspartic acid at all dosage levels tested increased phosphorus uptake by corn plants when no fertilizer was added. This indicates that a more efficient utilization of phosphorus sources existing in the soil has occurred. At the highest dosage level of polyaspartic acid, a 46.7% increase in phosphorus uptake by the corn plants was observed.

EXAMPLE 5

Effect of Polyaspartic Acid on Zinc Uptake in Early Sunglow Corn With No Added Fertilizer White corn (Early Sunglow) as was used in Examples 2, 3 and 4 was grown as before without added fertilizer. Again the same dosages of polyaspartic acid treatment for the corn plants was used as in Examples 2, and 4. After a 40-day growing period, the plants were harvested and zinc content of the plants was determined. Results from this study are listed in Table IV, below.

TABLE IV

EFFECT OF POLYASPARTIC ACID ON ZINC UPTAKE; EARLY SUNGLOW CORN; NO ADDED FERTILIZER; SINGLE TREATMENT/SOIL

| Dosage of Polyaspartic Acid Used | Zinc In Corn Plants, ppm | % Increase of Zinc In Corn Plants |
|---|---|---|
| 0 ppm | 29 | — |
| 1 ppm | 48 | 65.5 |
| 10 ppm | 45 | 55.2 |
| 100 ppm | 54 | 86.2 |
| 1000 ppm | 79 | 172 |

The above results from Table IV indicate that polyaspartic acid effectively increased the uptake of zinc in corn plants with no use of additional fertilizer. Even at a low dosage level of 1 ppm PA, a 65% increase in zinc uptake was observed. At a dosage of 1000 ppm of PA, a 172% increase in zinc uptake was found, further demonstrating the ability of polyaspartic acid to efficiently increase utilization of zinc in plant soil.

EXAMPLE 6

Effect of Polyaspartic Acid to Increase Plant Utilization of Limited Amounts of Nutrients Duckweed (*Lemna Minor L.*) was grown in tap water containing as nutrient media a solution of Peters™ 20-20-20 fertilizer[1] (3 g/1.2 L) and a ¼-strength solution (750 mg/1.2 L) with and without 50 ppm by weight polyaspartic acid (PA). The nutrient media were adjusted to pH value of about 6.0. The molecular weight (Mw) of the PA was about 3,000–5,000 (about 22 to about 40 repeating units).

[1]
Total Nitrogen (N) . . . 20%
   3.90% Ammoniacal Nitrogen
   6.15% Nitrate Nitrogen
   9.95% Urea Nitrogen
Available Phosphoric Acid ($P_2O_5$) . . . 20%
Soluble Potash ($K_2O$) . . . 20%
Derived from: Ammonium, Phosphate, Potassium Nitrate, Urea.
Commercially available from Grace-Sierra Horticultural Products Company,
1001 Yosemite Drive,
Milpitas, Calif. 95035.

A single duckweed plant at the three-frond stage was placed in each flask. The flasks were then incubated under continuous light (500 lux) at 28°±2° C. for 21 days.

After 21 days, the plants were harvested, oven-dried, and weighed. Results show that nutrient reduction by 75% reduced plant weight by 74%, and that (a) no significant reduction in plant growth was found when PA was present in the medium with 25% nutrients indicating a more efficient use of a limited amount of nutrients and (b) plant growth was enhanced when PA was present in the medium with 100% nutrients. The results are presented in Table V, below. All reported values represent 3 to 5 replicates.

TABLE V

RESULTS

| | Plant dry wt.-milligrams (mg) | | | |
|---|---|---|---|---|
| Treatment | Expt. A | Expt. B | Average | % Change |
| 100% Nutrients | 16.5 | 17.7 | 16.6 | 0 |
| 100% Nutrients + PA | 21.3 | 22.2 | 21.7 | 31 |
| 25% Nutrients | 4.7 | 4.0 | 4.4 | –74 |
| 25% Nutrients + PA | 15.2 | 16.7 | 16.0 | 0 |

EXAMPLE 7

Effect of Polyaspartic Acid on Biomass

The procedure described in Example 6, above, was followed except that a chemically defined nutrient medium having the composition described in U.S. Pat. No. 4,813,997 to Kinnersley et al. (Nickell's medium with Fe present as $Fe^{2+}$ chelated with EDTA) was used. The plants were grown in five replicate flasks, harvested after 21 days, and the combined dry weight of the harvested plants was determined. The content of potassium and phosphorus in the plants and in the spent media was determined as well. The observed results are presented in Table VI, below.

TABLE VI

CHANGES IN BIOMASS

| | Amount of Mineral (μg) Control/With PA | | |
|---|---|---|---|
| Treatment | Plant Biomass (mg) | Spent Media | Plants |
| 100% Nutrients/100% Nutrients + 50 ppm PA | 94.4/90.9 | | |
| Potassium (K) | | 11,610/11,740 | 1540/1530 |
| Phosphorus (P) | | 1170/1140 | 250/280 |
| 25% Nutrients/25% Nutrients + 50 ppm PA | 67.3/89.3 | | |
| Potassium (K) | | 2420/1170 | 990/1530 |
| Phosphorus (P) | | 334/322 | 125/173 |
| 12.5% Nutrients/12.5% Nutrients + 50 ppm PA | 54.1/62.7 | | |
| Potassium (K) | | 955/718 | 769/942 |
| Phosphorus (P) | | 190/192 | 89/111 |

The above results show that nutrient concentration reduced by 75% caused a 29% reduction in plant biomass (94.4–67.3) and a 36% reduction in the potassium content of plants (1540–990). However, in the same treatments containing polyaspartic acid the plant biomass was barely reduced (90.9–89.3), and the potassium content was unchanged. Analysis of the spent media showed much less potassium in the media containing PA. This data also indicates that the polymers had increased the uptake of potassium into plants.

The above results also show a remarkably good correlation between potassium content and plant-biomass as can be seen in Table VII, below.

TABLE VII

CORRELATION BETWEEN POTASSIUM CONTENT AND BIOMASS

| | Nutrients | | Nutrients + PA | |
|---|---|---|---|---|
| Nutrient Amount | Biomass (mg) | K (mg) | Biomass (mg) | K (mg) |
| 100% | 94.4 | 1.54 | 90.9 | 1.53 |
| 25% | 67.3 | 0.99 | 89.3 | 1.53 |
| 12.5% | 54.1 | 0.77 | 62.7 | 0.94 |

Potassium is the most important metal needed for plant growth, and is the principal metal component of most fertilizers. However, heretofore no agent was known able to simultaneously increase the growth and potassium content of plants.

EXAMPLE 8

Plant Content of Nutrients

The content of other nutrients in plants from the full strength and ¼-strength treatments described in Example 7, above, was determined. The observed results are set forth in Table VIII, below.

TABLE VIII

PLANT NUTRIENT CONTENT

Amount, micrograms (μg)

| Elements | 100% Nutrients | 25% Nutrients | 25% Nutrients + 50 ppm PA |
|---|---|---|---|
| Zn | 9.2 | 2.6 | 3.7 |
| Mg | 70 | 43 | 49 |
| Fe | 2.5 | 1.0 | 5.9 |
| Ca | 340 | 172 | 243 |
| Cu | 3.9 | 3.7 | 3.2 |
| Mn | 4.1 | 1.1 | 1.1 |
| Biomass, mg | 94.4 | 67.3 | 89.3 |

These results show that the content of most other minerals needed for plant growth was also greatly increased by the presence of PA. Particularly noteworthy is the substantial increase in the iron content at reduced nutrient level.

EXAMPLE 9

Effect of Polyaspartic Acid to Increase Plant Utilization of Limited Amounts of Nutrients Duckweed (*Lemna minor L.*) was grown in tap water under conditions described in Example 6, above, and containing as nutrient media a solution of Peters™ 20-20-20 fertilizer at full strength (100% nutrients), half strength (50% nutrients), and one-quarter strength (25% nutrients), with and without 50 ppm polyaspartic acid; molecular weight (Mw) 3000–5000.

The plants were harvested, oven dried, and weighed after 21 days. The average plant dry weight is reported in Table IX, below. All reported values represent 12 to 20 replicates.

TABLE IX

RESULTS

| Treatment | Average Plant Dry Wt. milligrams (mg) |
|---|---|
| 100% Nutrients | 15.5 |
| 100% Nutrients + PA | 20.2 |
| 50% Nutrients | 8.8 |
| 50% Nutrients + PA | 15.1 |
| 25% Nutrients | 3.7 |
| 25% Nutrients + PA | 9.9 |

Figure 5:
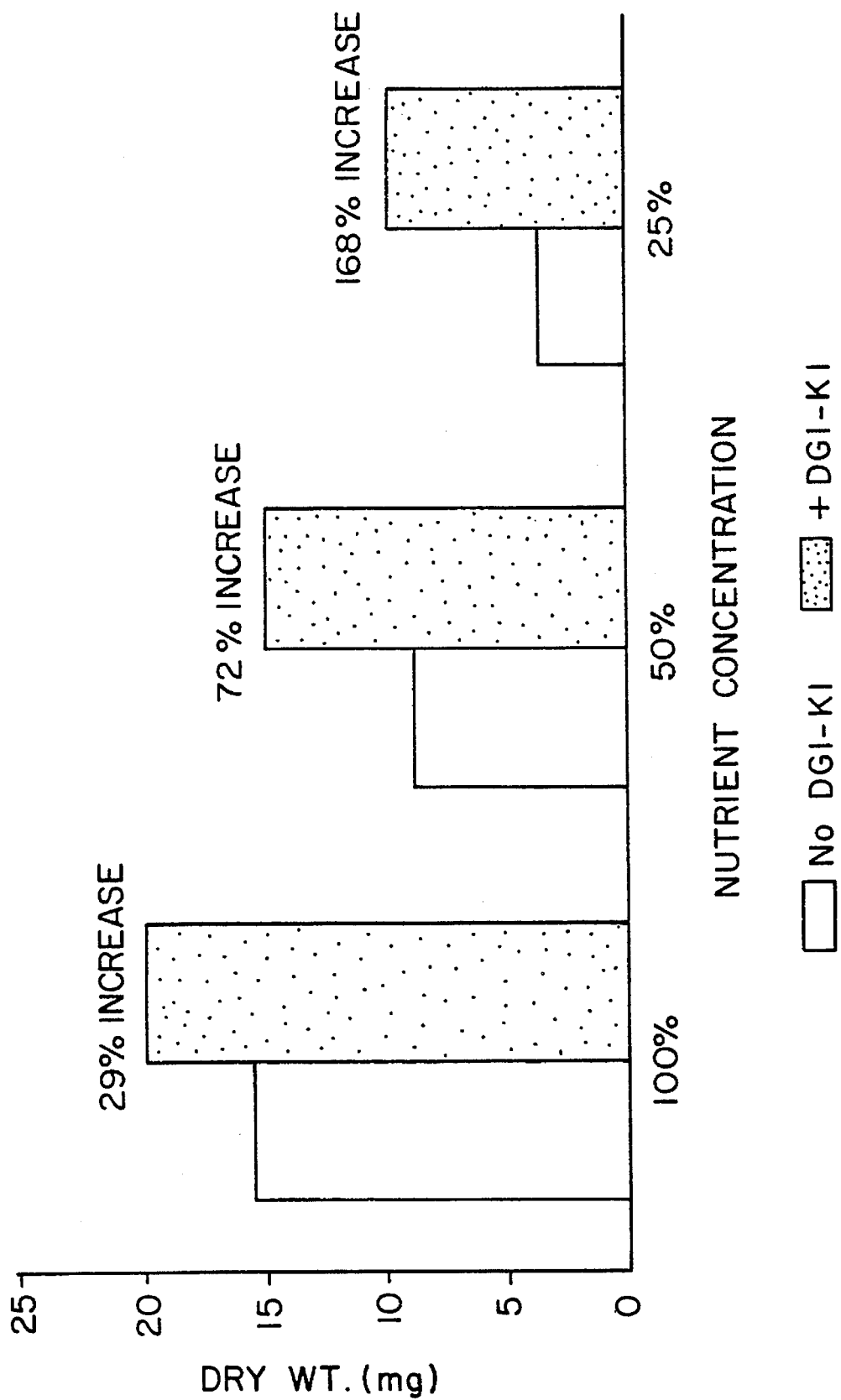
FIG. 5 is a graphical representation of growth enhancement with polyaspartic acid.

The foregoing results are depicted graphically in FIG. 5. These results show that the addition of polyaspartic acid (PA) permits a decrease in nutrient level by about 50% without a significant decrease in plant growth. From FIG. 5 it can also be seen that while the addition of PA to the nutrient solution increased plant growth at all nutrient levels, the effect of PA was much greater at the relatively lower levels of nutrients. Specifically, an increase in plant growth of about 168% was noted when PA was added to a 25% nutrient solution, and an increase of about 29% was noted when PA was added to a 200% nutrient solution. Therefore, when limited amounts of nutrients were available for plant growth, use of PA increased the efficiency of usage of these nutrients.

EXAMPLE 10

Effect of Polyaspartic Acid to Increase Bean Plant Utilization of Limited Amounts of Nutrients Garden beans (Mayo's Red Peanut Bush) were grown in the greenhouse in gallon pots filled with Fafard 3B potting soil. Ten pots were given 50 ml of a 7,500 ppm solution of Peters™ 20-20-20 nutrient. Twenty pots were given 50 ml of a 2,500 ppm Peters™ nutrient solution, and 10 of these pots were also given four weekly treatments of 50 ml aliquots of a 1 ppm solution of PA in water. When the bean plants flowered, they were taken outside for insect pollination. The beans that grew were harvested. The weight of beans on each plant was then determined. Results in Table X, below, show that PA increased reproductive growth results in a greater weight yield of beans from each plant. The increase in bean yield in the ⅓ fertilizer treatment with PA compared to the fertilizer alone, was statistically significant with Duncan's multiple range test.

TABLE X

YIELD OF BEANS

| Treatment | Average Fresh Weight of Beans/Plant, g |
|---|---|
| 100% Nutrients | 6.4 |
| 33% Nutrients | 3.9 |
| 33% nutrients + 1 ppm PA | 7.2 |

The foregoing data show that when one-third the regular nutrient level was used along with 1 ppm of PA, the average fresh weight of bean/plant increased by 85%. This was a greater yield than was obtained when the 100% nutrient level was used. Under the conditions of limited nutrient availability, use of PA increased the efficiency of nutrient utilization resulting in increased bean yields.

EXAMPLE 11

Effect of Polyaspartic Acid to Increase Rapeseed Plant Utilization of Limited Amounts of Nutrients A fast growing variety of rapeseed (*Brasica rapus*) was obtained from the Crucifer Genetics Cooperative at the University of Wisconsin. This variety was grown in 9-cm pots in a greenhouse. Pots were given 50 ml of a full strength solution of Peters™ 20-20-20 nutrient (7,500 ppm) in water, or the same volume of a 3,750 ppm solution in water. Some of the pots were given 50 ml of a 2 or 20 ppm solution of PA in water as a single treatment. Plants were pollinated by hand when they flowered. Mature seed pods were harvested. The observed results are reported in Table XI, below.

TABLE XI

RAPSEED HARVEST

| Treatment | Average # Pods per Plant | Average Dyr Weight of Pods per Plant, mg |
|---|---|---|
| Full Nutrient | 3.8 | 202 |
| 50% Nutrient | 2.9 | 174 |
| 50% Nutrient + 2 ppm PA | 4.8 | 283 |
| 50% Nutrient + 20 ppm PA | 5.2 | 290 |
| Full Nutrient + 2 ppm PA | 5.0 | 271 |

The above results show that average grain yield was higher in plants given PA than in plants receiving nutrient alone. PA increased grain yield in plants given both full and ½ strength nutrient. In many plants yield was higher for plants given ½ strength nutrient +2 ppm PA than in plants receiving full fertilizer alone. This result shows that use of PA increased the efficiency of utilization of a limited amount of nutrients available to the rapeseed plants.

EXAMPLE 12

Effect of Polyaspartic Acid on Duckweed Plants Grown in Tap Water

Duckweed was grown in tap water and in tap water solutions of PA following the procedure described in Example 6, above. Table XII, below, presents the compositions of the aqueous growth medium and the observed corresponding results. In each growth medium containing nutrients, the nutrient was Peters™ 20-20-20, and in each solution containing PA, the concentration of PA was 50 ppm.

TABLE XII

EFFECT OF POLYASPARTIC ACID ON DUCKWEED PLANTS GROWN IN TAP WATER

| Aqueous Growth Medium | Plant Dry Wt. (mg) | % Change |
|---|---|---|
| A. Nutrient (2.2 g/L) | 37 | |
| Nutrient (2.2 g/L) + PA | 78 | 111 |
| B. Nutrient (1.1 g/L) | 18 | |
| Nutrient (1.1 g/L) + PA | 57 | 217 |
| C. Nutrient (0.55 g/L) | 17 | |
| Nutrient (0.55 g/L) + PA | 22 | 72 |
| D. Tap water only[1] | 20 | |
| Tap water + PA | 26 | 30 |

[1]There is some mineral content in tap water.

In the above table, each treatment dosage of nutrient combined with PA is compared to the same nutrient dosage without PA (the control) and % change in plant weight compared to the corresponding control is given. The above results show that PA was least effective at promoting plant growth when it was given with treatment D that has no added nutrients. If, in fact, PA was acting as a fertilizer, it should have been most effective (as measured by relative % change over control) when plants had no added nutrient for growth. Actually, the reverse was observed to be true. PA was only effective in promoting plant growth in conjunction with a real nutrient source. In treatment D, when no nutrient was added, use of PA still permitted increased plant growth by facilitating uptake of minerals from the tap water.

EXAMPLE 13

Effect of Polyaspartic Acid on Duckweed Plants Grown in De-ionized Water

Duckweed was grown in de-ionized water and in de-ionized water solution of PA following the procedure described in Example 6, above, except that the plants were harvested after four weeks instead of 21 days. Table XIII, below, presents the composition of the aqueous growth media that were used and the corresponding observed results. Because the biomass of each plant was so minimal, plants from eight replicate flasks of each treatment were combined to provide enough plant material to be weighed accurately.

TABLE XIII

EFFECT OF POLYASPARTIC ACID ON DUCKWEED PLANTS GROWN IN DE-IONIZED WATER

| Aqueous Growth Medium | Plant Dry Wt. (mg) | % Change |
|---|---|---|
| A. De-ionized water | 8 | |
| B. De-ionized water + PA (50 ppm) | 2 | −75 |

The above results show that PA did not increase plant growth when added to de-ionized water from which all minerals had been removed. This effect would not have been observed if PA was functioning as a fertilizer.

The experiments performed with duckweed plants as described in Examples 12 and 13, above, demonstrate (a) that the polyaspartic acid of this invention had minimal biological activity when supplied to plants grown in tap water and (b) that polyaspartic acid itself showed no nutrient or fertilizer activity with regard to these plants when the plants were grown in de-ionized water.

In U.S. Pat. No. 4,839,461 to Boehmke it is stated that K, Mg, and Ca salts of polyaspartic acid are suitable for use as fertilizers. No experimental evidence or examples are given to support this statement. The above experiments with Duckweed plant in tap water and de-ionized water show that polyaspartic acid itself does not act as a fertilizer. It is likely that if the Ca, K and Mg salts of polyaspartic acid act as fertilizers, this activity is due to the nutrient value of Ca, K and Mg ions themselves rather than polyaspartic acid.

EXAMPLE 14

Effect of Polyaspartic Acid on Corn Plants

White corn (*Zea mays L.*) seed (5145 Truckers Favorite; George W. Park Seed Co., Greenwood, S.C.) was planted in 8-cm black round pots with Fafard 3B potting soil. Each pot

15 was given 0.3 g, 0.15 g, or 0.075 g of Peters™ 20-20-20 nutrient. Five pots representing each treatment were kept as controls, five pots were given 50 ml of 5 ppm aqueous PA solution, and five pots 50 ml of a 500 ppm aqueous PA solution. After six weeks the plants were harvested, and the fresh weight and nitrogen content of the harvested plants was determined. The observed results are reported in Table XIV, below.

TABLE XIV

EFFECT OF POLYASPARTIC ACID ON CORN PLANTS

| Treatment | Fresh wt., g | Average N Content, mg |
|---|---|---|
| 100% Nutrients | 45.8 | 67.6 |
| 100% Nutrients + 5 ppm PA | 46.5 | 75.7 |
| 100% Nutrients + 500 ppm PA | 50.2 | 73.2 |
| 50% Nutrients | 34.7 | 40.5 |
| 50% Nutrients + 5 ppm PA | 45.6 | 57.6 |
| 50% Nutrients + 500 ppm PA | 38.6 | 49.6 |
| 25% Nutrients | 24.1 | 29.6 |
| 25% Nutrients + 5 ppm PA | 31.7 | 36.2 |
| 25% Nutrients + 500 ppm PA | 38.3 | 47.8 |

Above results show that PA enables plants to be grown with a 50% reduction in nutrients without showing any reduction in growth. Simultaneously with increasing the corn biomass, PA also increased the nitrogen content of the corn. Plants grown with 25% nutrients and 500 ppm PA contained more nitrogen than plants grown with 50% nutrients that were given twice the amount of nitrogen.

EXAMPLE 15

Environmental Stability of Polyaspartic Acid

A nutrient solution was made by adding Peters™ 20-20-20 nutrient (375 mg) to tap water (150 ml). The solution was divided into three aliquots. One 50-ml aliquot was maintained as a control. To another aliquot was added 1,000 ppm of polyaspartic acid, and 1000 ppm of lactic acid oligomer containing less than ten lactic acid residues and obtained by thermal condensation of 88% L-lactic acid by heating at 70° C. for 4 hours followed by heating under vacuum at 100° C. for 4 hours was added to the last 50-ml aliquot.

The turbidity of the samples were measured every day to ascertain the extent of microbial growth in each sample. Within a few days the solution containing the lactic acid oligomer had become milky, indicating microbial contamination. The sample containing polyaspartic acid remained substantially clear, even after 7 days. The observations are compiled in Table XV, below.

TABLE XV

TURBIDITY MEASUREMENTS

| | DAYS | | | | |
|---|---|---|---|---|---|
| | 1 | 2 | 3 | 4 | 5 |
| Control | 0 | 0 | 0 | 0 | 0 |
| Polyaspartic Acid | −0.04 | +0.25 | +0.26 | +0.40 | +0.95 |
| Lactic Acid Oligomer | −0.11 | +2.20 | +3.45 | +16.5 | +382.0 |

Results indicate that polyaspartic acid has a relatively longer life in the environment.

16

EXAMPLE 16

Nutrient Composition for Hydroponic Growing

An illustrative aqueous composition embodying the present invention and well suited for hydroponic farming is set forth in Table XVI, below.

TABLE XVI

HYDROPONIC GROWING MEDIUM

Nutrients, ppm by weight

| Nitrogen as N | 50 |
|---|---|
| Phosphorus as P | 48 |
| Potassium as K | 210 |
| Magnesium as Mg | 30 |
| Sulfates as $SO_4^{-2}$ | 117 |
| Sodium as Na | 3.619 |
| Chlorides as Cl | 0.040 |
| Iron as Fe | 3.000 |
| Zinc as Zn | .150 |
| Copper as Cu | .150 |
| Boron as B | .500 |
| Manganese as Mn | .500 |
| Molybdenum as Mo | .100 |
| Water, q.s. | |

We claim:

1. A method for enhancing a more efficient uptake and utilization of plant growth nutrients by supplying to the plant a polyaspartic acid either directly or hydrolyzed from polysuccinimide that is water soluble, has a weight average molecular weight (Mw) larger than 1500 and is a non-chelating, non-aromatic polymer that cannot be absorbed by the plant having one of the following structures:

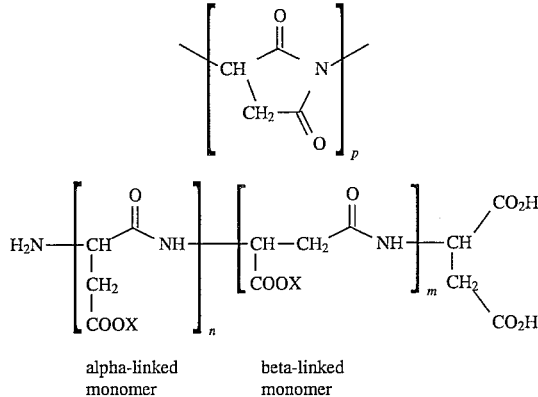

alpha-linked monomer   beta-linked monomer where $X=H^+$, $Na^+$, $NH_4^+$, $K^+$, $Ca^{++}$, $Mg^+$, $Zn^{++}$, $Co^{++}$, $Li^+$, $Ba^{++}$, $Fe^{++}$ and $Fe^{+++}$; n=0–100 mole % of aspartic acid mer units linked by α-peptide bonds or α form units; m=0–100 mole % of aspartic acid mer units linked by β-peptide bonds or β form units; and p=10–1000.

2. The method of claim 1, wherein the polyaspartic acid has m>50 % β form and n<50 mole % α form.

3. The method of claim 2, wherein the polyaspartic acid has m equal to 60–80 mole % β form.

4. The method of claim 3, wherein the polyaspartic acid has m equal to 70–80 mole % β form.

5. The method of claim 3, wherein the polyaspartic acid has m equal to 70–75 mole % β form and n equal to 25 to 30 mole % α form.

6. The method of claim 3, wherein the polyaspartic acid has a weight average molecular weight (Mw) within the range of 2000–100,000.

7. The method of claim 4, wherein the polyaspartic acid has a weight average molecular weight (Mw) within the range of 3000–5000.

8. The method of claim 5, wherein the polyaspartic acid has a weight average molecular weight (Mw) within the range of 3000–5000.

* * * * *